US008679312B2

(12) United States Patent
Inoue et al.

(10) Patent No.: US 8,679,312 B2
(45) Date of Patent: Mar. 25, 2014

(54) GAS SENSOR SYSTEM AND METHOD FOR CONTROLLING GAS SENSOR

(75) Inventors: Yoshinori Inoue, Nagoya (JP); Norikazu Ieda, Ichinomiya (JP)

(73) Assignee: NGK Spark Plug Co., Ltd., Aichi (JP)

( * ) Notice: Subject to any disclaimer, the term of this patent is extended or adjusted under 35 U.S.C. 154(b) by 710 days.

(21) Appl. No.: 12/618,955

(22) Filed: Nov. 16, 2009

(65) Prior Publication Data

US 2010/0122568 A1    May 20, 2010

(30) Foreign Application Priority Data

Nov. 17, 2008 (JP) ................................. 2008-293187

(51) Int. Cl.
*G01N 27/419* (2006.01)

(52) U.S. Cl.
USPC ........... 204/425; 204/426; 204/427; 204/428; 204/429; 73/23.31; 73/23.32

(58) Field of Classification Search
USPC ....................... 204/424–429; 73/23.31–23.32
See application file for complete search history.

(56) References Cited

U.S. PATENT DOCUMENTS 4,875,990 A * 10/1989 Kodachi et al. ............... 204/408
6,453,724 B1 * 9/2002 Kawase et al. ............... 73/23.31

FOREIGN PATENT DOCUMENTS

DE      3786127 T2    12/1993
JP     10-300720 A    11/1998

OTHER PUBLICATIONS

Baunach et al., "Sauberes Abgas durch Keramiksensoren", Physik Journal 5 (2006) No. 5, pp. 33-38.
Communication dated Feb. 7, 2013 from the German Patent Office in counterpart German application No. 10 2009 053 642.6.

* cited by examiner

*Primary Examiner* — Bach Dinh
(74) *Attorney, Agent, or Firm* — Sughrue Mion, PLLC

(57) ABSTRACT

A gas sensor system including a gas sensor; a current control unit; a constant control unit; and a temperature acquisition unit. The gas sensor includes a measurement chamber, a pump cell and an electromotive force cell. The current control unit performs feedback control on current flowing through the pump cell in response to the voltage of the electromotive force cell and in accordance with a control constant which characterizes the feedback control. Further, the constant control unit changes the control constant of the feedback control in accordance with a value (for example, a resistance value of the electromotive force cell) corresponding to the temperature of the gas sensor.

12 Claims, 10 Drawing Sheets

GAS SENSOR SYSTEM AND METHOD FOR CONTROLLING GAS SENSOR

BACKGROUND OF THE INVENTION

1. Field of the Invention

The present invention relates to a gas sensor system and a method for controlling a gas sensor.

2. Description of the Related Art

Hitherto, a gas sensor has been used for detection of specific gas components contained in the exhaust gas or the like of an internal combustion engine, or for measurement of the concentration of specific gas components. As such a gas sensor, a sensor is known that uses a reference cell and a detection cell, each having a zirconia solid electrolyte. In this sensor, the current flowing through the detection cell is controlled so that an electromotive force of the reference cell becomes constant. In this regard, a technique is known for controlling the current in a time-division manner.

[Patent Document 1]
Japanese Unexamined Patent Application Publication No. H10-300720-A

3. Problems to be Solved by the Invention:

When a gas sensor system is used for engine control, a control (for example, air-fuel ratio control) using a sensor output is desirably started as soon as possible after starting the engine in order to improve the accuracy of the engine control. On the other hand, when a sensor is used in which sensor elements are heated to a target temperature by a heater, it takes some time until the temperature of the sensor elements achieve the target temperature from the initial time of heating. In this case, the frequency characteristics of the gas sensor will change depending on the temperature of the sensor elements. However, sufficient studies have not yet been conducted with regard to control of the gas sensor in consideration of the temperature dependence of the frequency characteristics.

SUMMARY OF THE INVENTION

The present invention was made to solve the above-described problems at least in part, and an object thereof is to provide a technique that enables control of the gas sensor in consideration of the temperature dependence of frequency characteristics.

According to a first aspect (1), the above object of the present invention has been achieved by providing a gas sensor system, comprising: a gas sensor; a current control unit; a constant control unit; and an acquisition unit that acquires a corresponding temperature value which is a value corresponding to the temperature of the gas sensor, wherein: the gas sensor comprises: a measurement chamber into which a measurement target gas is introduced; a pump cell comprising, a first outer electrode, a first inner electrode that is exposed to the measurement chamber, and a first solid electrolyte that is interposed between the first outer electrode and the first inner electrode; and an electromotive force cell comprising a second outer electrode, a second inner electrode that is exposed to the measurement chamber, and a second solid electrolyte that is interposed between the second outer electrode and the second inner electrode; the current control unit performs feedback control on the current flowing through the pump cell in response to the voltage of the electromotive force cell and in accordance with a control constant which characterizes the feedback control; and, the constant control unit changes the control constant of the feedback control based on the corresponding temperature value.

According to this configuration, since the control constant is changed based on the corresponding temperature value of the gas sensor, it is possible to perform feedback control so as to adapt to the frequency characteristics of the gas sensor, which will change depending on the temperature of the gas sensor. As a result, it is possible to control the gas sensor in consideration of the temperature dependence of the frequency characteristics.

Further, in a preferred embodiment (2) according to (1) above, the gas sensor system further comprises a heater that is used for raising the temperature of the gas sensor to a target temperature; and, the constant control unit adopts: a first control constant when the corresponding temperature value indicates that the temperature of the gas sensor is within a first temperature range where a threshold temperature lower than the target temperature is an upper limit of the first temperature range; and a second control constant different from the first control constant when the corresponding temperature value indicates that the temperature of the gas sensor is within a second temperature range, the second temperature range including the target temperature and where a temperature higher than the threshold temperature is a lower limit of the second temperature range.

According to this configuration, since it is possible to use a control constant that is suitable for the temperature in each of the first temperature range and the second temperature range, it is possible to control the gas sensor in consideration of the temperature dependence of the frequency characteristics. In particular, according to this configuration, even when the sensor temperature is in a temperature range lower than the target temperature, it is possible to begin sensor measurements.

Further, in a preferred embodiment (3) according to any of (1) and (2) above, the current control unit comprises: a plurality of circuit elements that may be differently configured to define different control constants; and an analog computation circuit that executes computation for the feedback control based on a control constant defined by the circuit elements; and, the constant control unit comprises a switch that changes the control constant by switching a connection state between the analog computation circuit and the plurality of circuit elements.

According to this configuration, since it is possible to appropriately change the control constant of the computation by the analog computation circuit, it is possible to control the gas sensor in consideration of the temperature dependence of the frequency characteristics.

Further, in a preferred embodiment (4) according to any of (1) and (2) above, the current control unit comprises a computation unit that executes digital computation for the feedback control based on a constant value representing the control constant; and, the constant control unit changes the constant value used for the digital computation.

According to this configuration, since it is possible to appropriately change the constant value used for the digital computation, it is possible to control the gas sensor in consideration of the temperature dependence of the frequency characteristics.

Further, in a preferred embodiment (5) according to any of (1) to (4) above, the acquisition unit acquires, as the corresponding temperature value, an indicative value that correlates with a resistance value of the electromotive force cell; and, the constant control unit changes the control constant in accordance with the indicative value.

According to this configuration, since the control constant is changed in accordance with the indicative value that correlates with the resistance value of the electromotive force cell, and which changes depending on the temperature of the gas sensor, it is possible to control the gas sensor in consideration of the temperature dependence of the frequency characteristics.

In a preferred embodiment (6) according to any of (1) to (5) above, the current control unit performs a feedback control on the current flowing through the pump cell so that the voltage of the electromotive force cell becomes a target voltage.

According to this configuration, in a system in which the current flowing through the pump cell is subject to feedback control so that the voltage of the electromotive force cell becomes the target voltage, it is possible to control the gas sensor in consideration of the temperature dependence of the frequency characteristics.

According to second aspect (7), the present invention provides a method for controlling a gas sensor, wherein: the gas sensor comprises: a measurement chamber into which a measurement target gas is introduced; a pump cell comprising, a first outer electrode, a first inner electrode that is exposed to the measurement chamber, and a first solid electrolyte that is interposed between the first outer electrode and the first inner electrode; and an electromotive force cell comprising, a second outer electrode, a second inner electrode that is exposed to the measurement chamber, and a second solid electrolyte that is interposed between the second outer electrode and the second inner electrode; and, the method comprises: performing feedback control on current flowing through the pump cell in response to the voltage of the electromotive force cell and in accordance with a control constant which characterizes the feedback control; acquiring a corresponding temperature value which is a value corresponding to the temperature of the gas sensor; and changing the control constant of the feedback control in accordance with the corresponding temperature value.

In a preferred embodiment (8) according to (7) above, the method further comprises raising the temperature of the gas sensor to a target temperature by means of a heater; and, wherein the step of changing the control constant comprises: adopting a first control constant when the corresponding temperature value indicates that the temperature of the gas sensor is within a first temperature range where a threshold temperature lower than the target temperature is an upper limit of the first temperature range; and adopts a second control constant different from the first control constant when the corresponding temperature value indicates that the temperature of the gas sensor is within a second temperature range, the second temperature range including the target temperature and where a temperature higher than the threshold temperature is a lower limit of the second temperature range.

In a preferred embodiment (9) according to (7) and (8) above, an analog computation circuit executes computation for the feedback control based on a control constant, which control constant is defined by a plurality of circuit elements that may be differently configured to define different control constants; and, the step of changing the control constant comprises switching a connection state between the analog computation circuit and the plurality of circuit elements.

In a preferred embodiment (10) according to (7) and (8) above, a computation unit executes digital computation for the feedback control based on a constant value representing the control constant; and, the step of changing the control constant comprises changing the constant value used for the digital computation.

In a preferred embodiment (11) according to any of (7) to (10) above, the step of acquiring the corresponding temperature value comprises acquiring, as the corresponding temperature value, an indicative value that correlates with a resistance value of the electromotive force cell; and, the step of changing the control constant comprises changing the control constant in accordance with the indicative value.

In a preferred embodiment (12) according to any of (7) to (11) above, the step of performing feedback control on the current comprises performing feedback control on the current flowing through the pump cell so that the voltage of the electromotive force cell becomes a target voltage.

BRIEF DESCRIPTION OF THE DRAWINGS

Illustrative aspects of the invention will be described in detail with reference to the following figures wherein.

DETAILED DESCRIPTION OF THE PREFERRED EMBODIMENTS

The present invention will now be described in greater detail with reference to the drawings. However, the present invention should not be construed as being limited thereto.

A. First Embodiment

Figure 1:
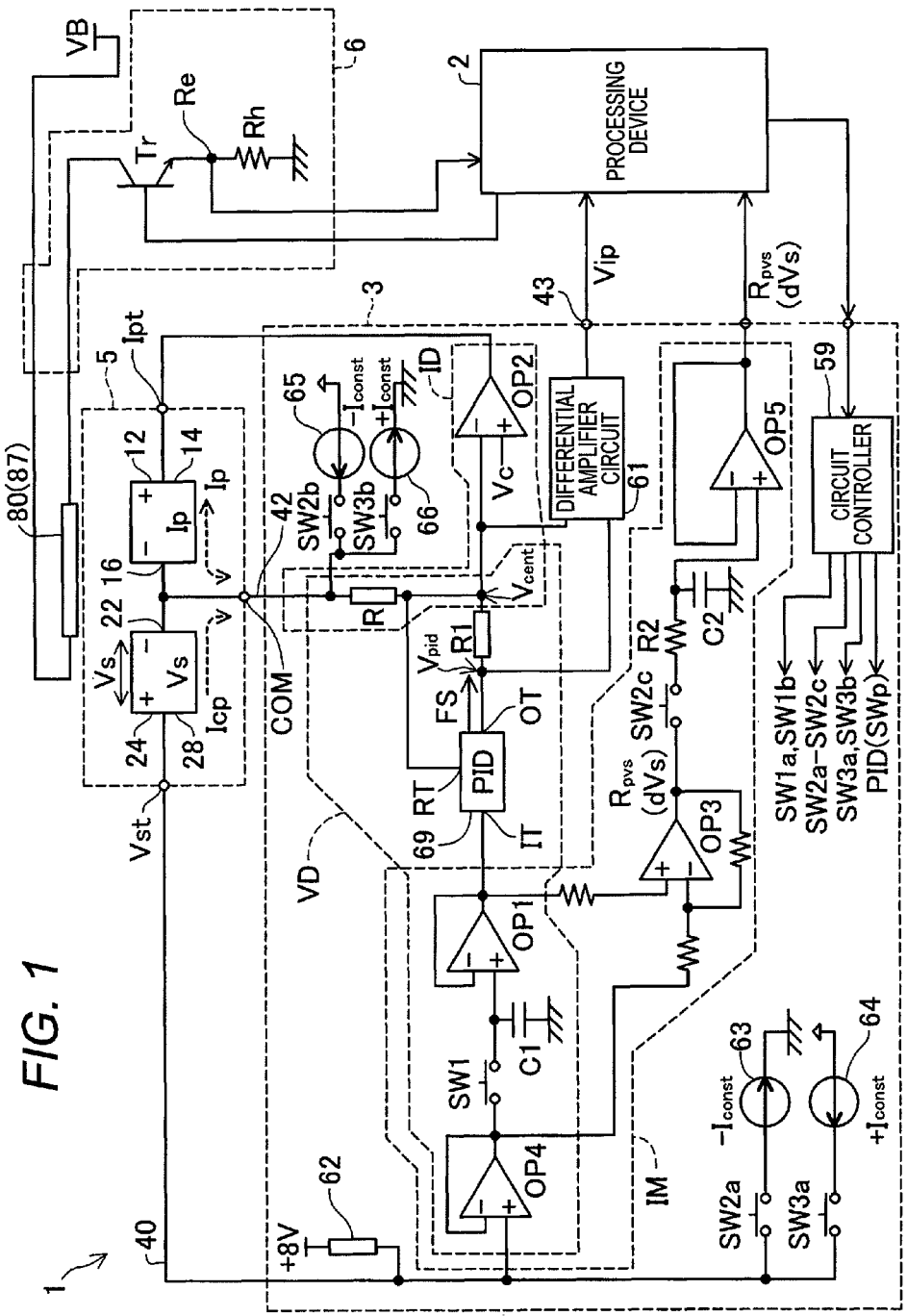
FIG. 1 is an explanatory view illustrating a gas sensor system 1 according to an embodiment of the present invention.

FIG. 1 is an explanatory view illustrating a gas sensor system 1 according to an embodiment of the present invention. The gas sensor system 1 includes a gas sensor 5, a heater 80 that heats the gas sensor 5, a detection circuit 3 that is connected to the gas sensor 5, a heater control circuit 6 that controls the heater 80, and a processing device 2 that controls the respective circuits 3 and 6. The gas sensor system 1 outputs an air-fuel ratio (A/F) of an air-fuel mixture supplied to an internal combustion engine. The output air-fuel ratio is used to control the amount of fuel injection, for example. In the present embodiment, a gasoline engine is used as the internal combustion engine.

Figure 2:
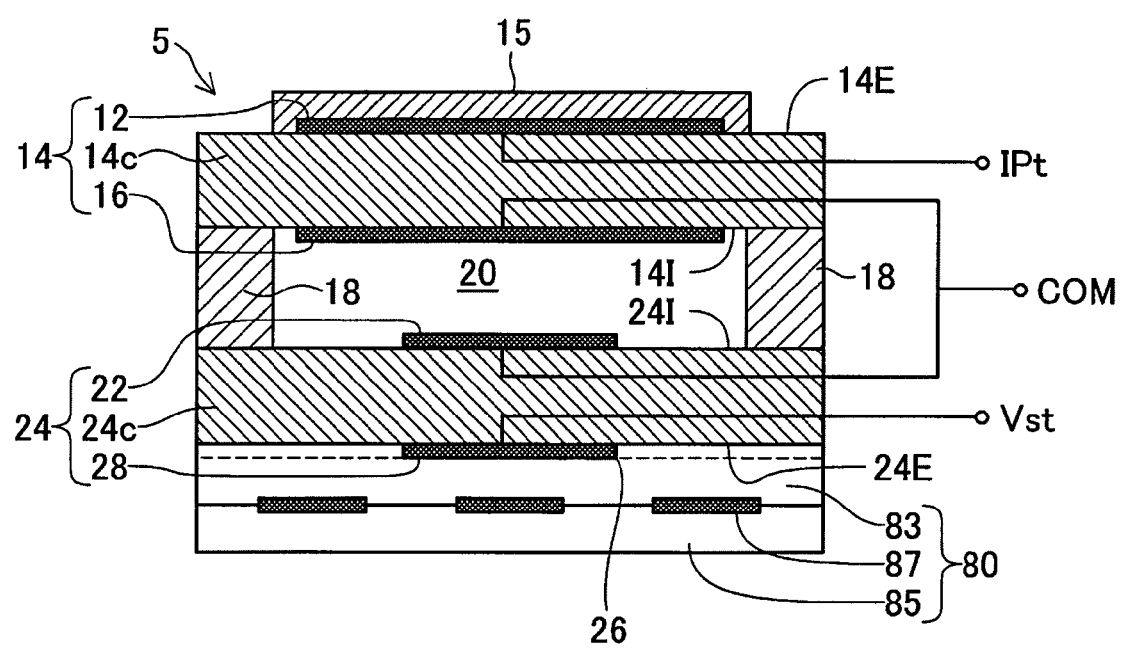
FIG. 2 is a simplified cross-sectional view illustrating the configuration of a gas sensor 5.

FIG. 2 is a simplified cross-sectional view illustrating the configuration of the gas sensor 5. The gas sensor 5 is a laminated body in which a pump cell 14, a porous diffusion layer 18, and an electromotive force cell 24 are laminated in this order. In the present embodiment, the gas sensor 5 is installed in a flow path (not illustrated) of the exhaust gas of the internal combustion engine and is used for measuring an air-fuel ratio (A/F). Moreover, a heater 80 is installed in the gas sensor 5.

The pump cell 14 includes an electrolyte layer 14c, an outer electrode 12 that is provided on one surface 14E of the electrolyte layer 14c, and an inner electrode 16 that is provided on the other surface 14I of the electrolyte layer 14c. The electrolyte layer 14c is interposed between the outer electrode 12 and the inner electrode 16. The electrolyte layer 14c is formed by a solid electrolyte having oxygen ion conductivity. In the present embodiment, partially stabilized zirconia is used as the solid electrolyte. Each of the electrodes 12 and 16 are porous electrodes. In the present embodiment, each of the electrodes 12 and 16 are formed of platinum. The outer electrode 12 is connected to a first terminal Ipt. Moreover, the whole outer electrode 12 is covered with a protection layer 15. The protection layer 15 is formed of a porous material such as ceramic. The protection layer 15 is disposed in the flow path of a measurement target gas (in the present embodiment, the exhaust gas). The exhaust gas can reach the outer electrode 12 through the protection layer 15. Moreover, the protection layer 15 suppresses poisoning of the outer electrode 12.

The electromotive force cell 24 includes an electrolyte layer 24c, an outer electrode 28 that is provided on one surface 24E of the electrolyte layer 24c, and an inner electrode 22 that is provided on the other surface 24I of the electrolyte layer 24c. The electrolyte layer 24c is interposed between the inner electrode 22 and the outer electrode 28. The electrolyte layer 24c is formed of the same solid electrolyte as the electrolyte layer 14c. Each of the electrodes 22 and 28 are porous electrodes like electrodes 12 and 16. The outer electrode 28 is connected to a second terminal Vst.

The inner surface 14I of the electrolyte layer 14c of the pump cell 14 opposes the inner surface 24I of the electrolyte layer 24c of the electromotive force cell 24. The porous diffusion layer 18 is interposed between these inner surfaces 14I and 24I. The porous diffusion layer 18 has a ring-shaped porous wall that surrounds a space between the inner surfaces 14I and 24I along the edges thereof. The porous diffusion layer 18 has a measurement chamber 20 defined therein that is surrounded by the porous wall, the electrolyte layer 14c and the electrolyte layer 24c. The porous diffusion layer 18 is disposed in the flow path of the measurement target gas. The measurement target gas is introduced into the measurement chamber 20 through the porous diffusion layer 18. Therefore, the porous diffusion layer 18 functions as a gas inflow portion. Various porous materials such as ceramic can be used as the material of the porous diffusion layer 18. In the present embodiment, the porous diffusion layer 18 diffuses the measurement target gas so as to limit its inflow speed.

The inner electrode 16 of the pump cell 14 and the inner electrode 22 of the electromotive force cell 24 are exposed to the measurement chamber 20. The electrodes 16 and 22 are electrically connected to each other and are also connected to a common third terminal COM.

The heater 80 is laminated on the outer surface 24E of the electrolyte layer 24c of the electromotive force cell 24. The heater 80 is configured such that a heater resistor 87 formed of a conductor is sandwiched by a pair of alumina sheets 83 and 85. The alumina sheet 83 is laminated on the outer surface 24E of the electrolyte layer 24c. The heater 80 raises the temperature of the gas sensor 5 (particularly, the electrolyte layers 14c and 24c) to activate the electrolyte layers 14c and 24c. In this way, oxygen ions are able to move in the electrolyte layers 14c and 24c. The configuration of the heater 80 is not limited to the configuration illustrated in FIG. 2, but may employ any configuration that can raise the temperature of the gas sensor 5 (particularly, the electrolyte layers 14c and 24c).

The alumina sheet 83 of the heater 80 covers the entire outer electrode 28 of the electromotive force cell 24 so as to obstruct the outer electrode 28. The inner space (porosity) of the outer electrode 28 (porous electrode) functions as a reference oxygen chamber 26 (described in greater detail below).

As illustrated in FIG. 1, one end of the heater resistor 87 of the heater 80 is connected to a DC power source VB (in the present embodiment, the DC power source VB is a 12-V DC power source). The other end of the heater resistor 87 is connected to the heater control circuit 6.

The heater control circuit 6 has a switching transistor Tr and a ground resistor Rh. The series circuit composed of the transistor Tr and the resistor Rh is connected to the heater resistor 87. The processing device 2 supplies a driving signal to the transistor Tr so as to control the On/Off state of the transistor Tr. When the transistor Tr is turned On, current flows through the heater resistor 87 and the heater 80 produces heat. When the transistor Tr is turned Off, current stops flowing into the heater resistor 87 and the heater 80 stops producing heat. The processing device 2 controls the On/Off state of the transistor Tr so as to control the heat produced by the heater 80, namely the temperature of the gas sensor 5. A node Re between the transistor Tr and the resistor Rh is connected to the processing device 2. The processing device 2 is able to regulate the current flowing through the heater 80 in accordance with the voltage at the node Re. The configuration of the heater control circuit 6 is not limited to the configuration illustrated in FIG. 1, but may employ any configuration that can control the heater 80.

Figure 3:
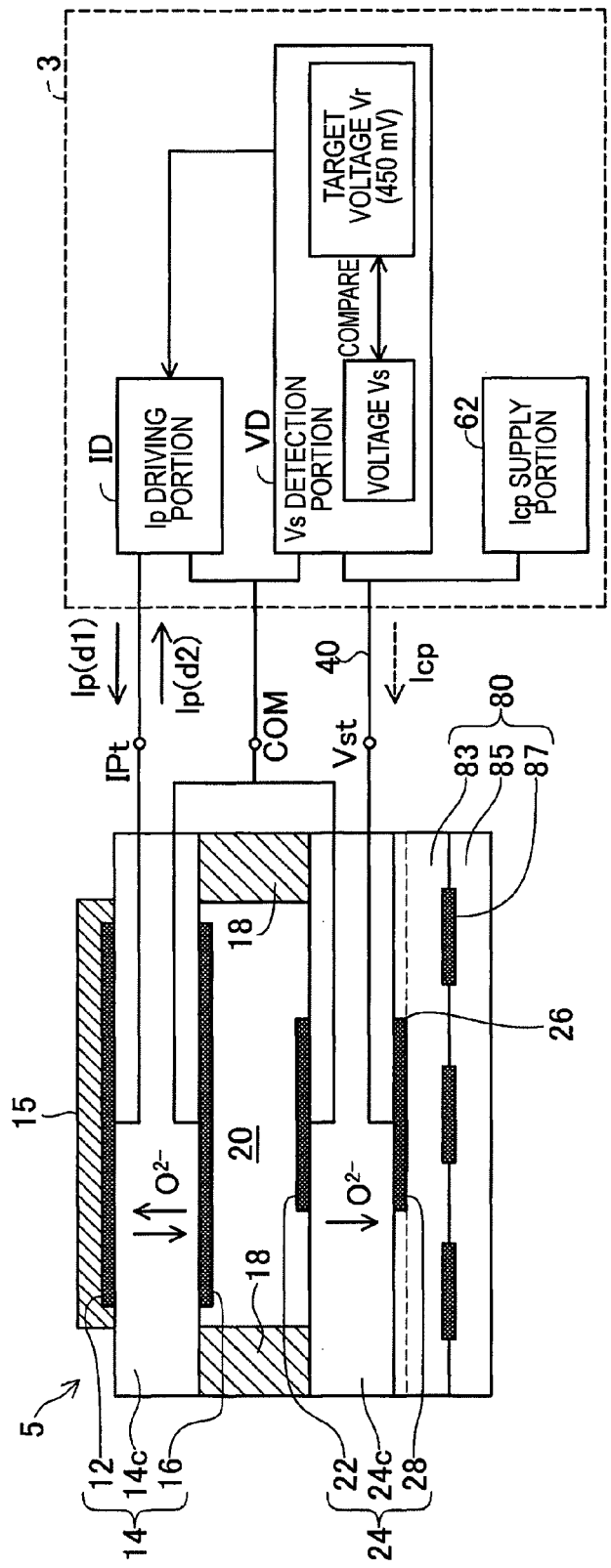
FIG. 3 is a simplified view of the gas sensor system 1.

FIG. 3 is a simplified view of the gas sensor system 1. In FIG. 3, the gas sensor 5 and the detection circuit 3 are illustrated in simplified form.

A constant current circuit 62 (FIGS. 1 and 3) is connected to the second terminal Vst via an energizing path 40. The constant current circuit 62 supplies a constant small current Icp which flows through the electromotive force cell 24. Therefore, the constant current circuit 62 functions as a current (Icp) supplying portion.

The current Icp flows from the outer electrode 28 to the inner electrode 22 so as to move (transport) oxygen from the measurement chamber 20 to the outer electrode 28 through the electrolyte layer 24c. The oxygen that has moved through the electrolyte layer 24c accumulates in the pores (the reference oxygen chamber 26) of the outer electrode 28. Since the constant current circuit 62 continuously supplies the current Icp, the oxygen concentration of the reference oxygen chamber 26 increases to a predetermined concentration which is substantially determined by the current Icp. Moreover, the oxygen concentration of the reference oxygen chamber 26 is maintained at the predetermined concentration. The reference oxygen chamber 26 serves as an oxygen concentration reference. The outer electrode 28 exposed to the reference oxygen chamber 26 serves as a reference electrode. The current Icp is preferably set so that the oxygen concentration in the reference oxygen chamber 26 becomes greater than the concentration of oxygen remaining in the exhaust gas.

The oxygen concentration is maintained at the predetermined concentration when the current Icp is supplied in a usual manner. This is because oxygen gradually leaks from the reference oxygen chamber 26 to the outside (that is, to the outside of the gas sensor 5). The path of such a leak may be the gap extending along the energizing path connecting the outer electrode 28 and the second terminal Vst.

A driving portion ID of current Ip is connected between the third terminal COM and the first terminal Ipt (namely, between the inner electrode 16 and the outer electrode 12 of the pump cell 14). The current Ip is current that flows through the pump cell 14. When the current Ip flows from the outer electrode 12 to the inner electrode 16, oxygen moves from the inner electrode 16 to the outer electrode 12 through the electrolyte layer 14c (this direction of the current Ip is referred to as the "first direction d1"). As a result, the oxygen concentration in the measurement chamber 20 decreases. To the contrary, when the current Ip flows from the inner electrode 16 to the outer electrode 12, oxygen moves from the outer electrode 12 to the inner electrode 16 through the electrolyte layer 14c (this direction of the current Ip is referred to as the "second direction d2"). As a result, the oxygen concentration in the measurement chamber 20 increases. In either case, the amount of oxygen moved per unit period of time is substantially proportional to the absolute value of the current Ip.

The driving portion ID is able to control the oxygen concentration in the measurement chamber 20 by supplying the current Ip through the pump cell 14. Particularly, the driving portion ID is able to increase and decrease the oxygen concentration in the measurement chamber 20 by changing the direction of the current Ip. In this way, the pump cell 14 is able to pump oxygen into the measurement chamber 20 and pump oxygen out of the measurement chamber 20. The details of the driving portion ID will be described below.

A detection portion VD of voltage Vs is connected between the second terminal Vst and the third terminal COM (namely, between the outer electrode 28 and the inner electrode 22 of the electromotive force cell 24). The voltage Vs is the voltage between the electrodes 22 and 28 of the electromotive force cell 24. The detection portion VD performs feedback control on the driving portion ID (namely, the current Ip) so that the voltage Vs becomes a predetermined target voltage Vr (in the present embodiment, 450 mV). The details of the detection portion VD will be described below. The detection portion VD and the driving portion ID collectively correspond to the "current control unit" of the invention.

Figure 4A:
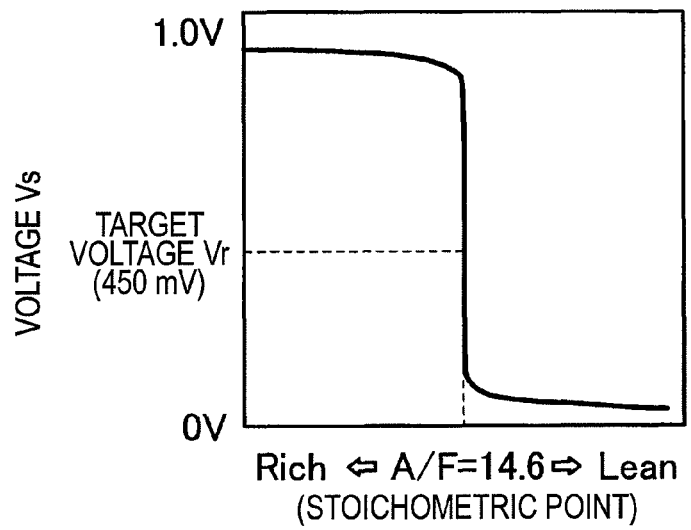
FIGS. 4A and 4B are graphs illustrating the relationship between the voltage Vs and the air-fuel ratio and the relationship between the current Ip and the air-fuel ratio.

FIG. 4A is a graph illustrating the relationship between the voltage Vs and the air-fuel ratio (A/F). The horizontal axis represents the air-fuel ratio (A/F) and the vertical axis represents the voltage Vs. The electromotive force cell 24 (FIG. 3) produces a larger electromotive force as the difference in the oxygen concentration between the two electrodes 22 and 28 increases (namely, the difference between the oxygen concentration in the reference oxygen chamber 26 and the oxygen concentration in the measurement chamber 20). This graph represents the voltage Vs when there is no oxygen pumping by the pump cell 14 (FIG. 3).

When the air-fuel ratio is higher than the theoretical air-fuel ratio (namely, when the air-fuel mixture is lean), a relatively large amount of oxygen remains in the exhaust gas, and thus, the oxygen concentration difference will decrease. As a result, the voltage Vs has a low value that corresponds to the oxygen concentration in the exhaust gas. In that case, the voltage Vs will be lower than the target voltage Vr.

When the air-fuel ratio is lower than the theoretical air-fuel ratio (namely, when the air-fuel mixture is rich), the oxygen concentration in the exhaust gas is low, and thus, the oxygen concentration difference will increase. As a result, the voltage Vs will increase. In this case, the voltage Vs will be higher than the target voltage Vr, and the voltage Vs in the present embodiment increases to about 1 V. Particularly, in the present embodiment, catalyst (platinum) is contained in the electrodes 16 and 22 in the measurement chamber 20. This catalyst accelerates the reaction between the residual oxygen in the measurement chamber 20 and the components (for example, CO, HC, and $H_2$) which have not be been burned in the exhaust gas. As a result, the oxygen concentration in the measurement chamber 20 decreases considerably. In this way, when the air-fuel ratio is lower than the theoretical air-fuel ratio, the voltage Vs becomes remarkably higher than when the air-fuel ratio is higher than the theoretical air-fuel ratio. As illustrated in the drawing, the voltage Vs changes stepwise before and after the theoretical air-fuel ratio. The theoretical air-fuel ratio is also referred to as the stoichiometric ratio or stoichiomatic point. In a gasoline engine, the theoretical air-fuel ratio is about 14.6.

Figure 4B:
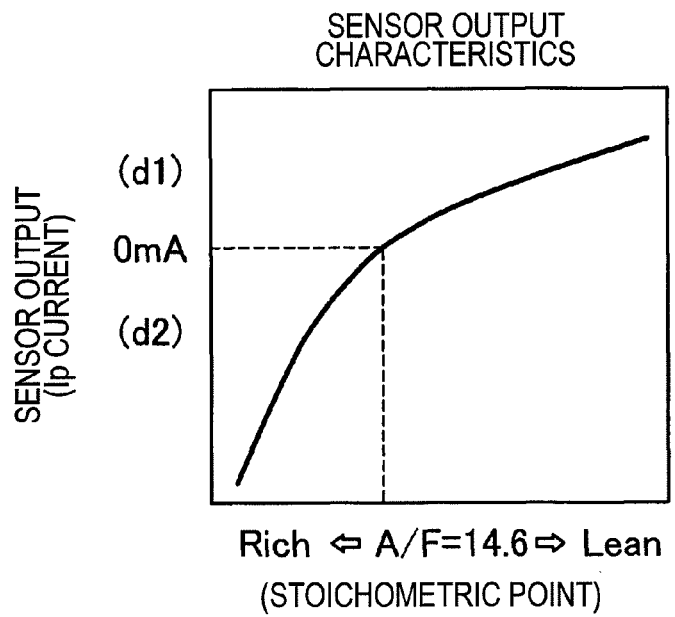

FIG. 4B is a graph illustrating the relationship between the current Ip and the air-fuel ratio (A/F). The horizontal axis represents the air-fuel ratio (A/F) and the vertical axis represents the current Ip. As described above, the current Ip is subject to feedback control so that the voltage Vs achieves the target voltage Vr.

When the air-fuel ratio is higher than the theoretical air-fuel ratio (when the air-fuel mixture is lean), the voltage Vs is lower than the target voltage Vr (FIG. 4A). In this case, the detection portion VD (FIG. 3) controls the driving portion ID to supply the current Ip in the first direction d1 so as to increase the voltage Vs to the target voltage Vr. In this way, since the oxygen concentration in the measurement chamber 20 decreases, the voltage Vs increases. Further, as the oxygen concentration of the exhaust gas introduced into the measurement chamber 20 increases (namely, as the air-fuel ratio increases), the amount of oxygen that needs to be moved from the measurement chamber 20 to the outer electrode 12 in order to increase the voltage Vs to the target voltage Vr increases. That is to say, as the air-fuel ratio increases, the absolute value of the current Ip increases. Moreover, since the amount of oxygen that needs to be moved per unit period of time is proportional to the oxygen concentration of the exhaust gas, the absolute value of the current Ip is substantially proportional to the air-fuel ratio.

When the air-fuel ratio is lower than the theoretical air-fuel ratio (when the air-fuel mixture is rich), the voltage Vs is higher than the target voltage Vr (FIG. 4A). In this case, the detection portion VD (FIG. 3) controls the driving portion ID to supply the current Ip in the second direction d2 so as to decrease the voltage Vs to the target voltage Vr. In this way, since the oxygen concentration in the measurement chamber 20 increases, the voltage Vs decreases. Here, as the air-fuel ratio decreases, the oxygen concentration in the exhaust gas decreases and the concentration of components (CO, HC, $H_2$, and the like) which have not been burned in the exhaust gas increases. When the reaction between these components and the oxygen is considered, as the air-fuel ratio decreases, the amount of oxygen required for increasing the oxygen concentration in the measurement chamber 20 increases. That is to say, as the air-fuel ratio decreases, the absolute value of the current Ip increases. Moreover, since the concentration of the subject components in the exhaust gas increases substantially in inverse proportion to the air-fuel ratio, the current Ip is substantially proportional to the air-fuel ratio.

As described above, the current Ip changes substantially in proportion to the air-fuel ratio over a wide range of the air-fuel ratio. Therefore, it is possible to specify the air-fuel ratio within a wide range in accordance with the current Ip.

Next, specific examples of the detection portion VD and the driving portion ID will be described. In FIG. 1, the detection portion VD and the driving portion ID are illustrated. As described below, the detection portion VD, the driving portion ID, and the gas sensor 5 are operated on the basis of a common reference voltage Vc (in the present embodiment, +3.6 V). As a result, the voltage of the third terminal COM is approximately maintained at the reference voltage Vc.

As illustrated in FIG. 1, the detection portion VD includes a fourth operational amplifier OP4, a first operational amplifier OP1, a feedback computation unit PID, a detection resistor R1, and a resistor R, which are connected in series. The fourth operational amplifier OP4 is connected to the second terminal Vst, and the resistor R is connected to the third terminal COM via an energizing path 42.

The fourth operational amplifier OP4 is configured as a voltage follower. The fourth operational amplifier OP4 outputs the same voltage as the voltage at the second terminal Vst. This voltage corresponds to the above-described voltage Vs. Specifically, the voltage of the second terminal Vst is the sum of the above-described voltage Vs and the reference voltage Vc. The output terminal of the fourth operational amplifier OP4 is connected to the first operational amplifier OP1 via a first switch SW1. The first operational amplifier OP1 is also connected to a capacitor C1. The first operational amplifier OP1 forms a sample-and-hold circuit in collaboration with the first switch SW1 and the capacitor C1. When the first switch SW1 is in the ON state, the first operational amplifier OP1 outputs the same voltage as the output voltage of the fourth operational amplifier OP4. The output terminal of the first operational amplifier OP1 is connected to the input terminal IT of the feedback computation unit PID. When the first switch SW1 switches to the OFF state, the first operational amplifier OP1 maintains the output voltage immediately prior to switching.

The feedback computation unit PID includes a reference terminal RT and an output terminal OT in addition to the input terminal IT. The output terminal OT is connected to a node Vpid that corresponds to one end of the detection resistor R1. The reference terminal RT is connected to a node Vcent that corresponds to the other end of the detection resistor R1. The node Vcent is connected to the resistor R and the inverting input terminal of a second operational amplifier OP2. The output terminal OT is connected to the inverting input terminal of the second operational amplifier OP2 via the detection resistor R1.

Figure 5:
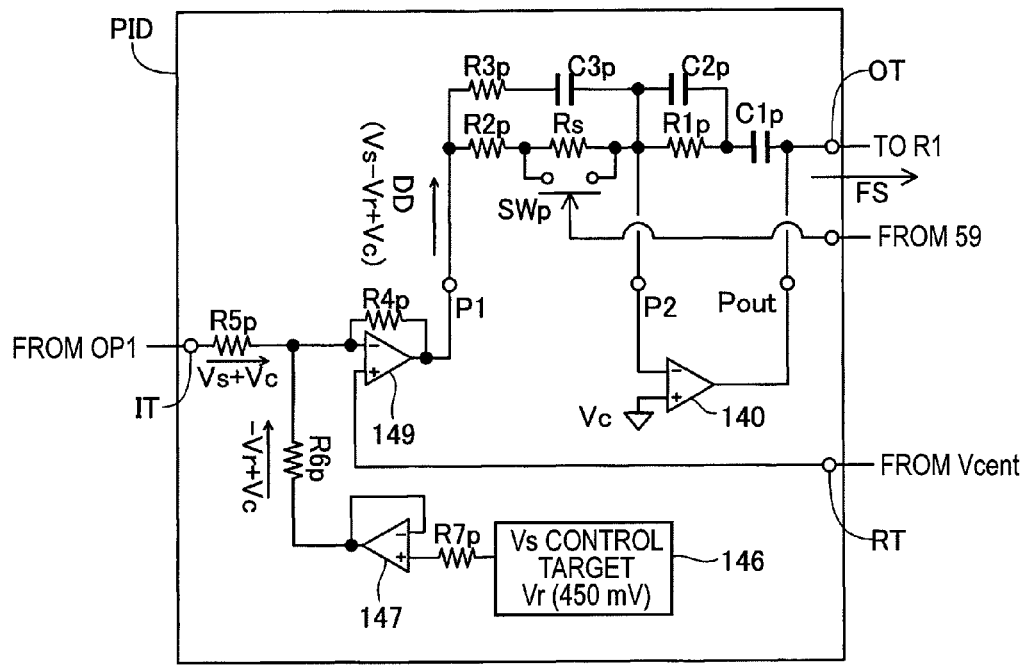
FIG. 5 is an explanatory view of a feedback computation unit PID.

FIG. 5 is an explanatory view of the feedback computation unit PID. The feedback computation unit PID includes three operational amplifiers 140, 147 and 149. The input terminal IT is connected to the inverting input terminal of the adding operational amplifier 149 via a resistor R5$p$. The adding operational amplifier 149 is configured as an adder circuit. The inverting input terminal of the adding operational amplifier 149 is connected to the output terminal of the reference operational amplifier 147 via a resistor R6$p$. The reference operational amplifier 147 is configured as a voltage follower. The reference operational amplifier 147 is connected to a target voltage output portion 146 via a resistor R7$p$. The target voltage output portion 146 outputs a negative target voltage Vr, and therefore the reference operational amplifier 147 configured as a voltage follower also outputs the negative target voltage Vr. In the present embodiment, the output voltage is a voltage obtained by subtracting the target voltage Vr from the reference voltage Vc.

The non-inverting input terminal of the adding operational amplifier 149 is connected to the reference terminal RT. The reference terminal RT is connected to the node Vcent (FIG. 1). Therefore, the adding operational amplifier 149 adds two signals (the voltage Vs and the negative target voltage Vr), which are supplied to the inverting input terminal, to the voltage (typically, the reference voltage Vc) of the node Vcent. As a result, the adding operational amplifier 149 outputs a signal that corresponds to a voltage obtained by subtracting the target voltage Vr from the voltage Vs. This signal is referred to as a "difference signal DD". Specifically, the difference signal DD has a voltage of "Vs−Vr+Vc." The output terminal of the adding operational amplifier 149 is connected to a first node P1 on the circuit.

On the circuit of the feedback computation unit PID illustrated in FIG. 5, a second node P2 and an output node Pout are depicted in addition to the first node P1. The second node P2 is connected to the inverting input terminal of the control operational amplifier 140, and the output node Pout is connected to the output terminal of the control operational amplifier 140. The non-inverting input terminal of the operational amplifier 140 is supplied with a predetermined reference voltage Vc.

Two circuits are connected between the first node P1 and the second node P2. One circuit is a series circuit composed of a capacitor C3$p$ and a resistor R3$p$. The other circuit is a series circuit composed of a resistor R2$p$ and a switch resistor Rs. A switch SWp is connected in parallel to the switch resistor Rs. The non-inverting input terminal of the control operational amplifier 140 is supplied with the difference signal DD via these circuits.

By turning On the switch SWp, the switch resistor Rs can be short-circuited. Therefore, by controlling the On/Off state of the switch SWp, it is possible to change the resistance value between the two nodes P1 and P2. In the present embodiment, the switch SWp is an analog switch. As for the switch SWp, a switching transistor such as, for example, an FET (Field Effect Transistor) can be used. The switch SWp is controlled by the processing device 2 with the aid of a circuit controller 59 in FIG. 1.

A series circuit composed of a resistor R1$p$ and a capacitor C1$p$ is connected between the second node P2 and the output node Pout. A capacitor C2$p$ is connected in parallel to the resistor R1$p$. The output signal of the control operational amplifier 140 is fed back to the inverting input terminal of the control operational amplifier 140 via these circuits.

The control operational amplifier 140 performs a so-called PID (Proportional-Integral-Derivative) computation with the aid of these circuit elements. As the result of this computation, the control operational amplifier 140 outputs a signal which corresponds to the difference signal DD supplied to the inverting input terminal (namely, the difference between the voltage Vs and the target voltage Vr). Hereinafter, the output signal is also referred to as feedback signal FS. The control operational amplifier 140 determines a change in the voltage of the feedback signal FS from the reference voltage Vc in accordance with a change in the voltage Vs from the target voltage Vr. In this manner, the voltage of the feedback signal FS changes from the reference voltage Vc in accordance with the difference between the voltage Vs and the target voltage Vr.

A control constant used for computation by the control operational amplifier 140 is determined by the circuit element connected between the two nodes P1 and P2 and the circuit element connected between the two nodes P2 and Pout. As described above, the resistance value between the two nods P1 and P2 can be changed by turning the switch SWp On/Off. In this manner, it is possible to change the constant used for the computation. The reason for changing the constant is described below.

The output terminal of the control operational amplifier 140 is connected to the output terminal OT. The feedback signal FS output from the output terminal OT is supplied to the inverting input terminal of the second operational amplifier OP2 via the detection resistor R1 (FIG. 1).

The second operational amplifier OP2 (FIG. 1) is one element of the driving portion ID. As illustrated in FIG. 1, the driving portion ID includes the resistor R and the second operational amplifier OP2 which are connected in series. The resistor R is connected to the inverting input terminal of the second operational amplifier OP2. The first terminal Ipt is connected to the output terminal of the second operational amplifier OP2.

The non-inverting input terminal of the second operational amplifier OP2 is supplied with the predetermined reference voltage Vc. The inverting input terminal of the second operational amplifier OP2 is supplied with the feedback signal FS via the detection resistor R1. The second operational amplifier OP2 controls the output signal in accordance with the difference between the reference voltage Vc and the voltage of the feedback signal FS.

As described above, the feedback computation unit PID (FIG. 5) determines the change in the voltage of the feedback signal FS from the reference voltage Vc in accordance with the change in the voltage Vs from the target voltage Vr. When the voltage Vs is higher than the target voltage Vr, the feedback computation unit PID determines the feedback signal FS so that the second operational amplifier OP2 outputs the current Ip in the second direction d2 (FIG. 3) (FIGS. 4A and 4B). When the voltage Vs is lower than the target voltage Vr, the feedback computation unit PID determines the feedback signal FS so that the second operational amplifier OP2 outputs the current Ip in the first direction d1. As a result, the current Ip is feedback-controlled so that the voltage Vs becomes the target voltage Vr.

The output terminal OT of the feedback computation unit PID is connected to the third terminal COM via the detection resistor R1 and the resistor R. As described above, the voltage of the feedback signal FS changes from the reference voltage Vc in accordance with the difference between the voltage Vs and the target voltage Vr. Therefore, the node Vcent between the detection resistor R1 and the resistor R or the third terminal COM is maintained approximately at the reference voltage Vc.

The current Ip that has been subjected to the feedback control is detected by the detection resistor R1. As illustrated in FIG. 1, a differential amplifier circuit 61 is connected to the detection resistor R1. The differential amplifier circuit 61 amplifies the voltage (the voltage between the node Vpid and the node Vcent) developed across the detection resistor R1. Then, the differential amplifier circuit 61 supplies the amplified output signal (hereinafter, also referred to as gas detection signal Vip) to the processing device 2 via a gas detection terminal 43. This voltage (the voltage between the nodes Vpid and Vcent) changes in accordance with the feedback signal FS. Moreover, the second operational amplifier OP2 controls the current Ip in accordance with the feedback signal FS. Therefore, it is possible to specify the magnitude and direction of the current Ip, namely the air-fuel ratio, in accordance with the gas detection signal Vip.

Figure 6:
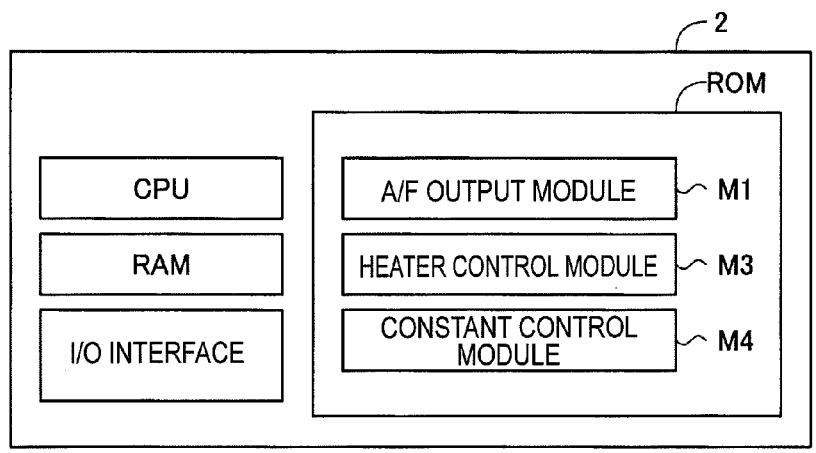
FIG. 6 is an explanatory view illustrating the configuration of a processing device 2.

FIG. 6 is an explanatory view illustrating the configuration of the processing device 2. The processing device 2 is a computer that has a CPU, a RAM, a ROM and an I/O interface. The ROM has stored therein an A/F output module M1, a heater control module M3, and a constant control module M4. These modules are programs executed by the CPU. Hereinafter, the act of the CPU executing processes in accordance with the modules is also expressed as "the modules executing the processes." The respective modules M1 to M4 transmit/receive data to/from each other via the RAM.

The A/F output module M1 specifies the air-fuel ratio in accordance with the gas detection signal Vip (FIG. 1). The corresponding relationship between the gas detection signal Vip and the air-fuel ratio is experimentally determined in advance. The A/F output module M1 supplies a specific air-fuel ratio to a controller (not illustrated) of an internal combustion engine.

The heater control module M3 supplies a driving signal to the heater control circuit 6 to raise the temperature of the gas sensor 5 to a predetermined target temperature. As the target temperature, a temperature within a range of 800 to 900° C., for example, can be employed.

The constant control module M4 changes the control constant of the feedback computation unit PID in accordance with the temperature of the gas sensor 5.

Figure 7:
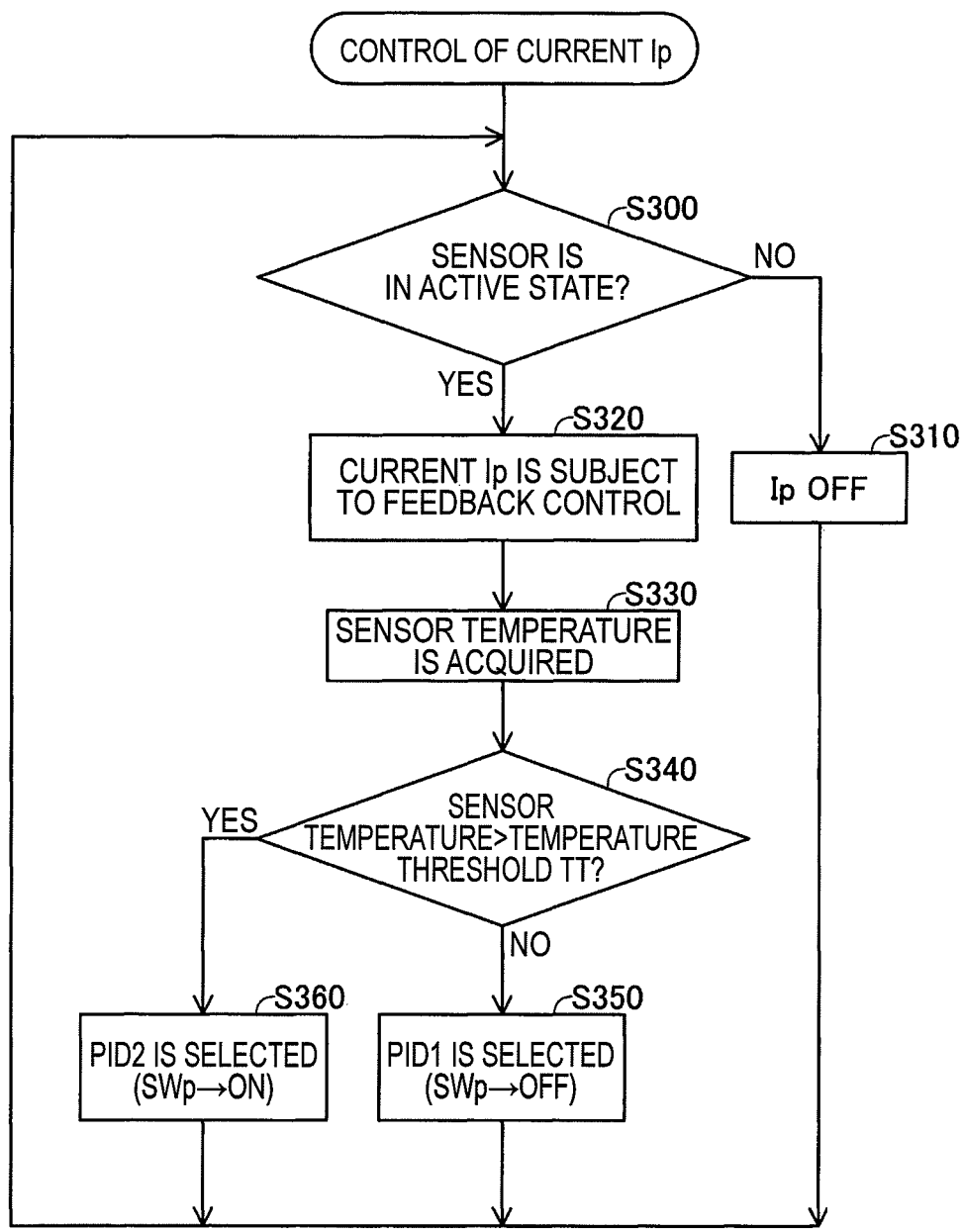
FIG. 7 is a flowchart illustrating the procedures for controlling the current Ip.

FIG. 7 is a flowchart illustrating the procedures for controlling the current Ip. The constant control module M4 (FIG. 6) starts the process of FIG. 7 at the time of starting the gas sensor system 1 (FIG. 1). At the time of starting the gas sensor system 1, the heater control module M3 starts a heater control process in order to raise the temperature of the gas sensor 5. The heater control process is described below.

First, in step S300, the constant control module M4 (FIG. 6) determines whether or not the gas sensor 5 (particularly, the electrolyte layers 14c and 24c) is in the active state. As the condition for determining that the gas sensor 5 is in the active state, an arbitrary condition can be employed. For example, a condition that a predetermined period of time has elapsed after the heater 80 (FIGS. 1 and 2) is turned on may be employed. Moreover, a condition that the temperature of the gas sensor 5 is higher than a predetermined active threshold value may be employed. As such an active threshold value, a temperature in the range of 500 to 600° C., for example, may be employed.

When a determination is made that the gas sensor 5 (FIG. 1) is not in the active state, the constant control module M4 (FIG. 6) turns off the current Ip in step S310. As a method for turning off the current Ip, an arbitrary method can be employed. For example, the constant control module M4 may turn off a power source of the second operational amplifier OP2. Moreover, a switch may be provided between the output terminal of the second operational amplifier OP2 and the first terminal Ipt, and the constant control module M4 may turn off the switch. When the current Ip is already turned off, the constant control module M4 ends the operation of step S310. Subsequent to step S310, the constant control module M4 returns to step S300.

When a determination is made that the gas sensor 5 (FIG. 1) is in the active state, the constant control module M4 (FIG. 6) begins feedback control of the current Ip in step S320. In step S320, an operation opposite that of step S310 is executed. In this way, the detection circuit 3 (FIG. 1) performs feedback control on the current Ip. When the control of the current Ip has already started, the constant control module M4 ends the operation of step S320.

In step S330, the constant control module M4 (FIG. 6) acquires the temperature of the gas sensor 5. The temperature acquisition method is described below.

In step S340, the constant control module M4 (FIG. 6) determines whether or not the temperature acquired in step S330 is higher than a predetermined threshold temperature TT. The temperature threshold TT is set to a value lower than the target temperature of the gas sensor 5 (for example, 700 to 800° C.).

When the temperature of the gas sensor 5 is equal to or lower than the threshold temperature TT, the constant control module M4 selects a first control constant PID1 in step S350. In the present embodiment, the constant control module M4 implements the first control constant PID1 by turning off the switch SWp in FIG. 5. The feedback computation unit PID performs computation in accordance with the first control constant PID1. The first control constant PID1 is used in a temperature range equal to or lower than the threshold temperature TT. This temperature range corresponds to "first temperature range" of the invention. The minimum value of the temperature where a determination is made in step S300 that the gas sensor 5 is in the active state corresponds to the lower limit of the first temperature range. Moreover, the first control constant PID1 is experimentally determined in advance so that feedback control can be performed appropriately.

When the temperature of the gas sensor 5 is higher than the threshold temperature TT, the constant control module M4 selects a second control constant PID2 in step S360. In the present embodiment, the constant control module M4 implements the second control constant PID2 by turning on the switch SWp in FIG. 5. The feedback computation unit PID performs computation in accordance with the second control constant PID2. The second control constant PID2 is used in a temperature range higher than the threshold temperature TT. The second control constant PID2 is also used when the gas sensor is at the target temperature. This temperature range corresponds to "second temperature range" of the invention. In the present embodiment, the temperature of the gas sensor 5 is raised to the target temperature. Therefore, the target temperature is included in the second temperature range and may also correspond to the upper limit of the second temperature range. Moreover, the second control constant PID2 is experimentally determined in advance so that feedback control can be performed appropriately.

Figure 8A:
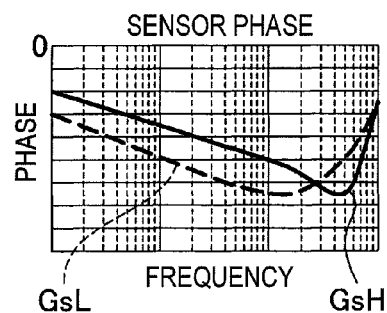
FIGS. 8A to 8F are graphs illustrating frequency characteristics.
Figure 8D:
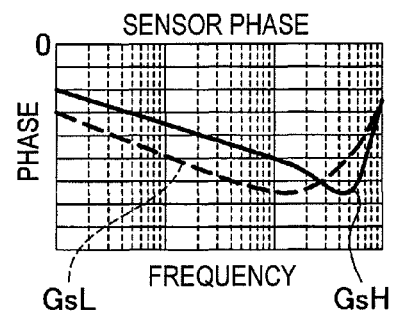
Figure 8B:
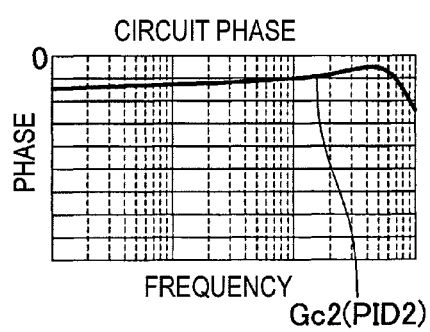
Figure 8E:
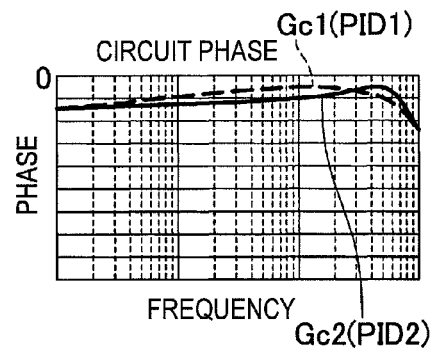
Figure 8C:
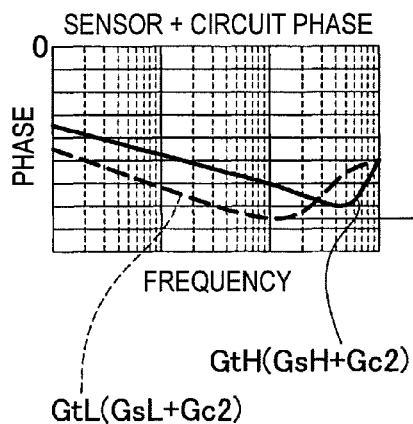

FIGS. 8A to 8F are graphs illustrating frequency characteristics of the gas sensor. The horizontal axis represents the frequency and the vertical axis represents the phase delay. The upper end of the vertical axis denotes points where the phase delay is zero, and the phase delay increases at points more distant from the upper end. FIGS. 8A to 8C correspond to comparative examples and FIGS. 8D to 8F correspond to the present embodiment. In the comparative examples, the first control constant PID1 (FIG. 7) is not used but the second control constant PID2 is used regardless of the temperature.

FIG. 8A illustrates the frequency characteristics of the gas sensor 5 (FIG. 1). The phase delay of the gas sensor 5 represents the delay of the change in the voltage Vs relative to the change in the current Ip. The solid graph GsH illustrates an example of the frequency characteristics when the temperature of the gas sensor 5 is at the target temperature, and the broken graph GsL illustrates an example of the frequency characteristics when the temperature of the gas sensor 5 is lower than the temperature threshold TT. The active states of the electrolyte layers 14c and 24c change significantly depending on the temperature. Therefore, the frequency characteristics of the gas sensor 5 will also change depending on the temperature. In the example of FIG. 8A, when the temperature is low, the phase delay is large at low frequencies.

FIG. 8B illustrates the frequency characteristics of the detection circuit 3. The phase delay of the detection circuit 3 represents the delay of the change in the current Ip relative to the change in the voltage Vs. The solid graph Gc2 illustrates the frequency characteristics when the second control constant PID2 is used.

FIG. 8C illustrates the overall frequency characteristics (open-loop frequency characteristics) of the gas sensor 5 and the detection circuit 3. The solid graph GtH represents high temperature characteristics and the broken graph GtL represents low temperature characteristics. The high-temperature graph GtH is obtained by combining the above-described graphs GsH and Gc2. The low-temperature graph GtL is obtained by combining the above-described graphs GsL and Gc2. The second control constant PID2 is experimentally set in advance to a value that is appropriate during normal operation (namely, when the temperature of the gas sensor 5 is at the target temperature). Therefore, when the temperature is low, the phase delay is larger than when the temperature is high. As a result, since the phase margin is small when the temperature of the gas sensor 5 is low, the feedback control of the gas sensor system 1 is prone to oscillation.

Next, the present embodiment will be described. The graphs GsL and GsH illustrated in FIG. 8D are identical to the graphs GsL and GsH illustrated in FIG. 8A, respectively. FIG. 8E illustrates the frequency characteristics of the detection circuit 3. A first graph Gc1 is added to the second graph Gc2 illustrated in FIG. 8B. The first graph Gc1 illustrates the frequency characteristics when the first control constant PID1 is used. In the first graph Gc1, the phase delay is small at low frequencies as compared to the second graph Gc2.

Figure 8F:
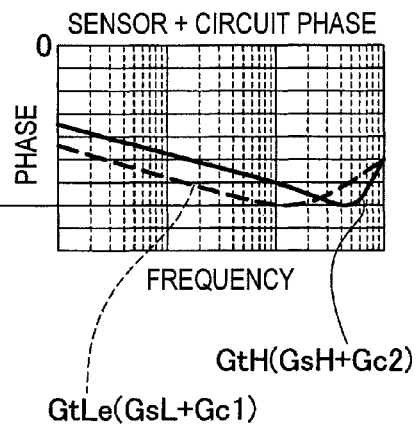

FIG. 8F illustrates the overall frequency characteristics of the gas sensor 5 and the detection circuit 3. The high-temperature graph GtH is identical to the graph GtH illustrated in FIG. 8C. The low-temperature graph GtLe is obtained by combining the graph GsL with the first graph Gc1 in place of the second graph Gc2. The first control constant PID1 is experimentally set in advance to a value that is appropriate when the temperature of the gas sensor 5 is lower than the threshold temperature TT. Therefore, when the temperature is low, the phase delay can be improved, namely decreased, by using the first control constant PID1 in place of the second control constant PID2. As a result, it is possible to stably use the gas sensor system 1 even when the temperature of the gas sensor 5 has not reached the target temperature after the gas sensor system 1 has been started. In this way, it is possible to perform the feedback control so as to adapt to the frequency characteristics of the gas sensor 5, which will change depending on the temperature.

The first control constant PID1 is implemented by turning off the switch SWp in FIG. 5. When the switch SWp is Off, the resistance value between the two nodes P1 and P2 increases by an amount of the switch resistor Rs. Moreover, the gain of the control operational amplifier 140 can be expressed by (Resistance value between P2 and Pout)/(Resistance value between P1 and P2). Therefore, the gain can be decreased by turning off the switch SWp. As the gain decreases, in many cases, the phase delay by the control operational amplifier 140 decreases. For these reasons, it is possible to decrease the phase delay by the control operational amplifier 140 by turning off the switch SWp. However, the responsiveness of the feedback control is considered to be good when the second control constant PID2 is used at high temperatures compared to when the first control constant PID1 is used at low temperatures.

Subsequent to steps S360 and S350 in FIG. 7, the constant control module M4 (FIG. 6) returns to step S300. Then, the constant control module M4 repeatedly executes the switching of control constants in accordance with the temperature. In this manner, in the present embodiment, it is possible to control the gas sensor 5 in consideration of the temperature dependence of the frequency characteristics of the gas sensor 5.

Figure 9:
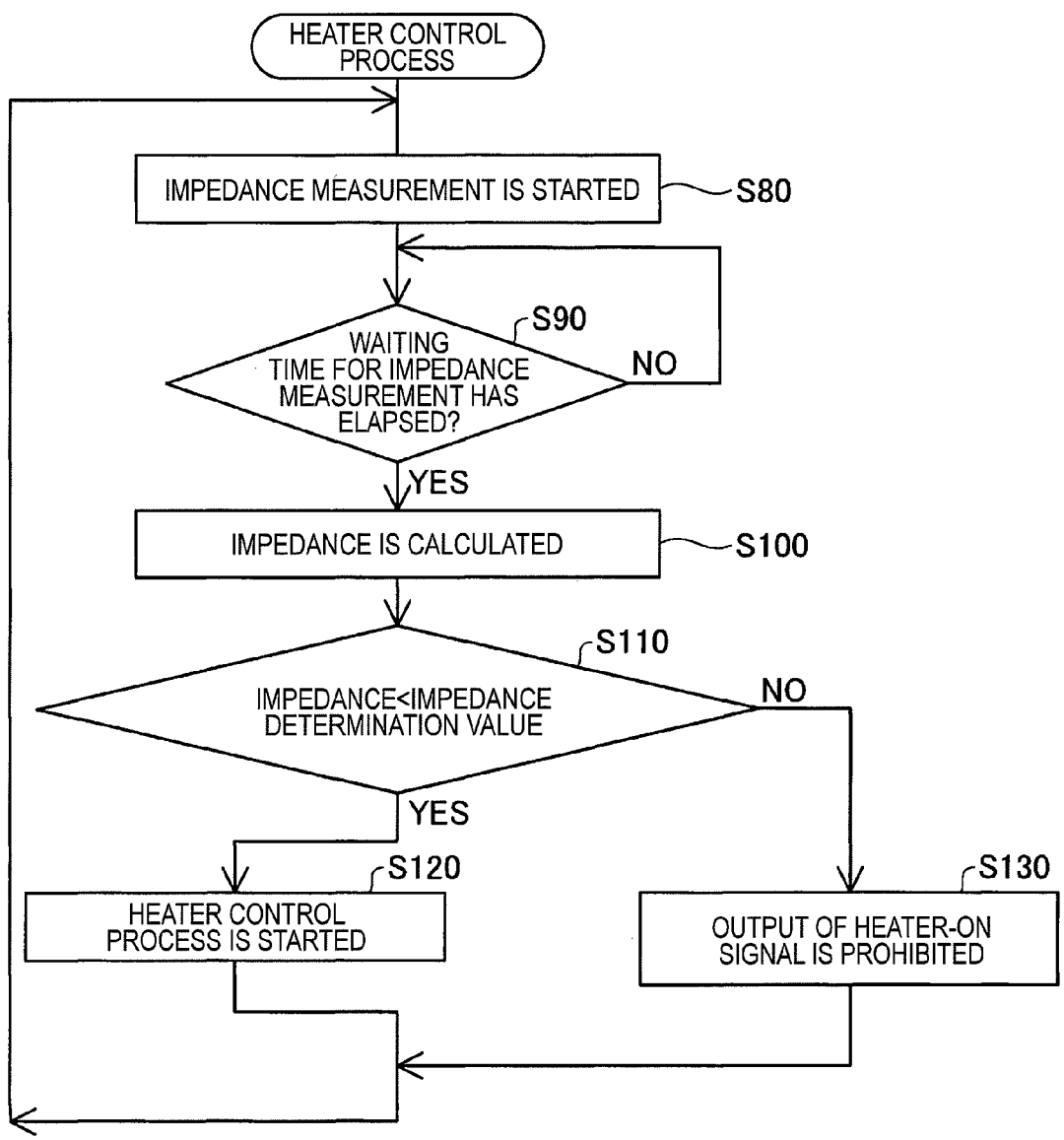
FIG. 9 is a flowchart illustrating procedures for a heater control process.

FIG. 9 is a flowchart illustrating the procedure for a heater control process. First, in step S80, the heater control module M3 (FIG. 6) instructs the circuit controller 59 (FIG. 1) to start measurement of the element impedance. The element impedance represents the impedance (particularly, the resistance value) of the electromotive force cell 24. The circuit controller 59 starts a process of measuring impedance in accordance with the instructions (this process is also referred to as a "voltage variation measurement process").

Figure 10:
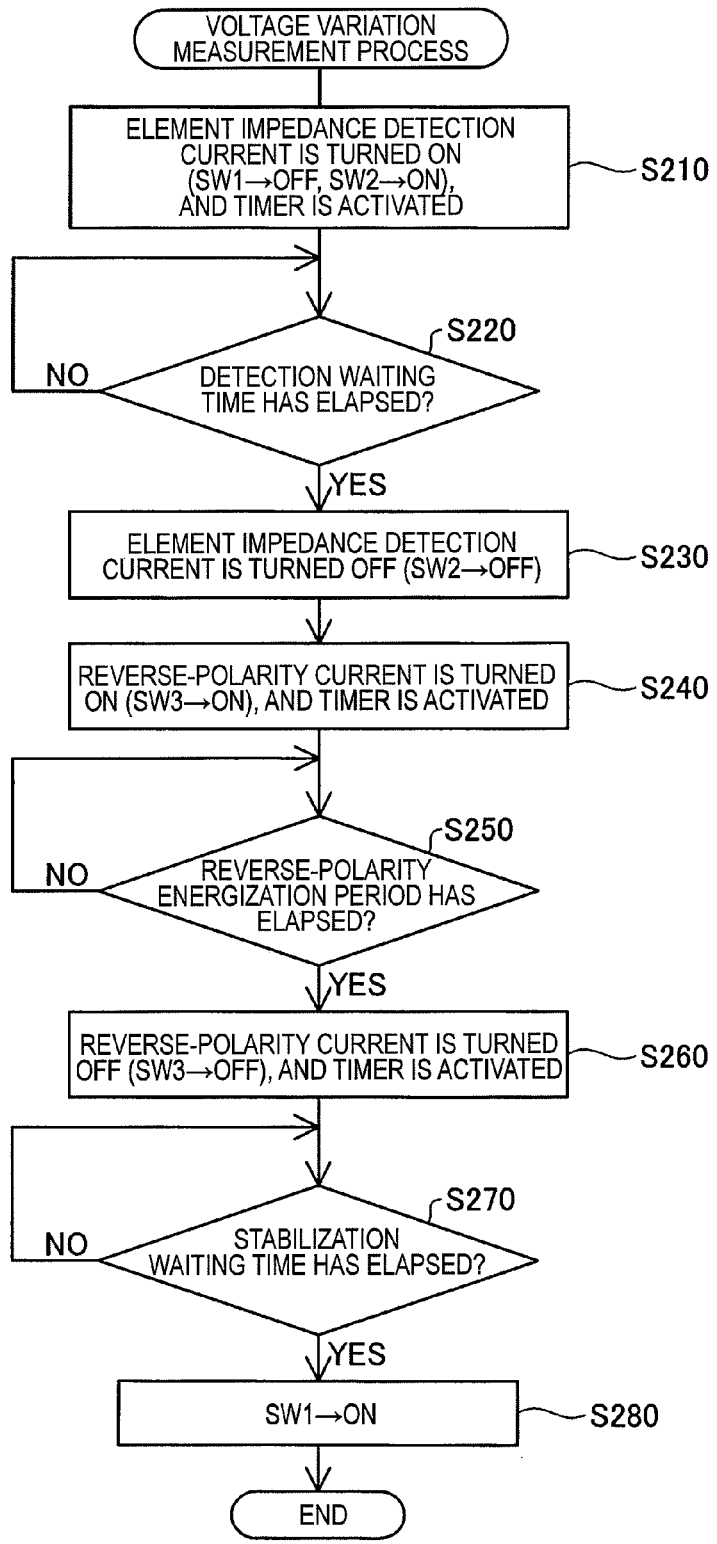
FIG. 10 is a flowchart illustrating procedures for a voltage variation measurement process.

FIG. 10 is a flowchart illustrating the procedures for the voltage variation measurement process. First, in step S210, the circuit controller 59 (FIG. 1) turns off the first switch SW1. By doing so, the fist operational amplifier OP1 maintains the voltage (corresponding to the voltage Vs) at the time of starting the operation of step S210. The output signal of the first operational amplifier OP1 is supplied to the non-inverting input terminal of the third operational amplifier OP3.

The circuit controller 59 (FIG. 1) turns on second switches SW2a to SW2c. The second terminal Vst (the energizing path 40) is connected to a constant current source 63 via the second switch SW2a. The third terminal COM is connected to a constant current source 65 via the second switch SW2b. By the turning on of the switches SW2a and SW2b, a constant current (−Iconst) is supplied through the electromotive force cell 24 (this current is also referred to as an "element impedance detection current" or simply as "detection current"). This current flows through the electromotive force cell 24 from the inner electrode 22 to the outer electrode 28. The fourth operational amplifier OP4 outputs the voltage (corresponding to the voltage Vs) during the energized state of the electromotive force cell 24. The output signal of the fourth operational amplifier OP4 is supplied to the inverting input terminal of the third operational amplifier OP3. The first operational amplifier OP1 maintains the voltage immediately before energization of the electromotive force cell 24.

The third operational amplifier OP3 outputs a signal Rpvs that represents a voltage difference dVs between the output signal from the first operational amplifier OP1 and the output signal from the fourth operational amplifier OP4. The voltage difference dVs represents a voltage required for supplying the constant current (−Iconst) through the electromotive force cell 24. The voltage difference dVs is proportional to the resistance value (the bulk resistance value) of the electromotive force cell 24. Therefore, the impedance signal Rpvs can be used as a signal representing the impedance (particularly, the resistance value) of the electromotive force cell 24. The impedance signal Rpvs correlates to the resistance value of the electromotive force cell 24. Moreover, the constant current sources 63 and 65 and the entire circuit IM from the fourth operational amplifier OP4 to the fifth operational amplifier OP5 correspond to an "acquisition unit" that acquires the impedance signal Rpvs.

The impedance signal Rpvs is supplied to the fifth operational amplifier OP5 via the second switch SW2c. The fifth operational amplifier OP5 forms a sample-and-hold circuit in collaboration with the resistor R2 and the capacitor C2.

In step S210 of FIG. 10, the circuit controller 59 (FIG. 1) activates a non-illustrated timer to start measurement of an elapsed time.

In step S220, the circuit controller 59 waits for a predetermined detection waiting time (in the present embodiment, 60 μsec). By doing so, the fifth operational amplifier OP5 can output the impedance signal Rpvs with certainty.

When the detection waiting time has elapsed, the circuit controller 59 (FIG. 1) turns off the second switches SW2a to SW2c in step S230. In this way, the electromotive force cell 24 is deenergized. Moreover, the fifth operational amplifier OP5 holds the impedance signal Rpvs and continuously supplies the impedance signal Rpvs to the processing device 2.

In step S240, the circuit controller 59 (FIG. 1) turns on third switches SW3a and SW3b. The second terminal Vst (the energizing path 40) is connected to the constant current source 64 via the third SW3a. The third terminal COM is connected to the constant current source 66 via the third switch SW3b. By the turning on of the switches SW3a and SW3b, a reverse current (+Iconst) in a direction opposite the above-described element impedance detection current is supplied through the electromotive force cell 24. Moreover, the circuit controller 59 activates a non-illustrated timer to start measurement of an elapsed time.

The reason for supplying the reverse current through the electromotive force cell 24 is described below. Depending on the alignment phenomenon of the electrolyte layer 24c due to the detection current, the electromotive force cell 24 may enter into a state in which it is unable to output an inner electromotive force reflecting the original oxygen concentration difference. By supplying the current in a direction opposite the detection current through the electromotive force cell 24, it is possible to reduce the time required for the electromotive force cell 24 to restore a normal state (a state of being able to output an inner electromotive force reflecting the oxygen concentration difference). Moreover, measurement of the oxygen concentration can be resumed in a short period of time after the impedance signal Rpvs is measured.

In step S250, the circuit controller 59 waits for a predetermined reverse energization period (in the present embodiment, 60 μsec). In this manner, the electromotive force cell 24 can appropriately restore its original state. In addition, the reverse energization period is preferably the same as the detection waiting time in order for the electromotive force cell 24 to restore its original state.

When the reverse energization period has elapsed, the circuit controller 59 turns off the third switches SW3a and SW3b in step S260. In this manner, the electromotive force cell 24 is deenergized. Moreover, the circuit controller 59 activates a non-illustrated timer to start measurement of an elapsed time.

In step S270, the circuit controller 59 waits for a predetermined stabilization waiting time (in the present embodiment, 600 μsec). The stabilization waiting time is preferably longer than the time required to restore a state in which the electromotive force cell 24 is able to output an inner electromotive force which reflects the oxygen concentration difference after the impedance signal Rpvs has been acquired. The stabilization waiting time may be determined experimentally.

When the stabilization waiting time has elapsed, the circuit controller 59 (FIG. 1) turns on the first switch SW1 in step S280. In this manner, the detection portion VD and the driving portion ID starts the above-described feedback control of the current Ip. In addition, the voltage variation measurement process ends.

Subsequent to step S80 in FIG. 9, the heater control module M3 (FIG. 6) waits for a measurement waiting time (in the present embodiment, 100 msec) in step S90. The voltage variation measurement process ends in the meantime.

When the measurement waiting time has elapsed, the heater control module M3 (FIG. 6) calculates the impedance of the electromotive force cell 24 from the impedance signal Rpvs in step S100. The corresponding relationship between the impedance signal Rpvs and the impedance may be determined in advance experimentally.

In step S110, the heater control module M3 determines whether or not the calculated impedance is smaller than a predetermined impedance determination value (in the present embodiment, 220 ohms). This determination is made so as to verify the connection state of the energizing line (for example, the energizing path 40) of the electromotive force cell 24.

When the calculated impedance is smaller than the impedance determination value, the heater control module M3 (FIG. 6) determines that the energizing line is in a normal condition. Then, the heater control module M3 supplies a driving signal to the heater control circuit 6 (FIG. 1) to control the heater 80 in step S120. In step S120, the heater 80 is controlled so that the calculated impedance becomes a predetermined target impedance. In general, as the temperature of the electrolyte layer 24c (FIG. 2) increases, the activity of the electrolyte layer 24c increases, and accordingly, the impedance (electrical resistance) of the electromotive force cell 24 decreases. Therefore, the impedance can be used as an indicator of temperature. In the present embodiment, the target impedance is set to a value that corresponds to the above-described target temperature. As the method for controlling the heater 80, various well-known methods can be employed. For example, PWM (Pulse Width Modulation) may be employed.

When the calculated impedance is equal to or higher than the impedance determination value, the heater control module M3 (FIG. 6) determines that the energizing line is in an abnormal condition. Then, the heater control module M3 prohibits the driving signal that turns on the heater 80 in step S130.

After each operation of steps S120 and S130 is performed, the heater control module M3 returns to step S80. Then, the heater control module M3 repeatedly executes the above-described operations and processes.

As described above, since the heater control module M3 (FIG. 6) controls the heater control circuit 6 so that the impedance of the gas sensor 5 becomes the target impedance, it is possible to appropriately maintain the temperature of the gas sensor 5 at the target temperature. Moreover, since the heater control module M3 repeatedly calculates the impedance of the gas sensor 5, it is possible to cope with a change in the temperature environment of the gas sensor 5.

As described above, the impedance of the gas sensor 5 (FIG. 1) correlates with the temperature of the gas sensor 5. Therefore, in the present embodiment, the constant control module M4 (FIG. 6) calculates the impedance of the gas sensor 5 from the impedance signal Rpvs and specifies the temperature of the gas sensor 5 from the impedance in step S330 of FIG. 7. Each of the corresponding relationship between the impedance signal Rpvs and the impedance and the corresponding relationship between the impedance and temperature may be experimentally determined in advance. As described above, the impedance signal Rpvs is periodically updated in accordance with the procedures in FIGS. 9 and 10. In step S330 of FIG. 7, the constant control module M4 calculates the temperature in accordance with the latest impedance signal Rpvs. Then, the constant control module M4 controls (changes) the control constant in accordance with the calculated temperature (S340 to S360). In this way, the constant control module M4 controls the control constant in accordance with the impedance signal Rpvs. Alternatively, the constant control module M4 may change the control constant by comparing the impedance with an impedance threshold value without converting the impedance (resistance value) into a temperature value. The impedance threshold value is set in advance to a value that corresponds to the threshold temperature TT. In this case, the constant control module M4 controls (changes) the control constant in accordance with the temperature. Specifically, although in the embodiment, the sensor temperature is calculated from the impedance in step S330, and the sensor temperature is compared with the threshold temperature TT in step S340, the impedance itself may be compared with an impedance threshold value (a value corresponding to the threshold temperature (TT)) in step S340. In this case, the flow proceeds to step S360 when the impedance is smaller than the impedance threshold value, whereas the flow proceeds to step S350 when the impedance is larger than the impedance threshold value. The value of the impedance signal Rpvs may be used, per se, as the impedance used for the control. Alternatively, the impedance may be calculated from the impedance signal Rpvs and the calculated impedance may be used for the control.

B. Second Embodiment

Figure 11:
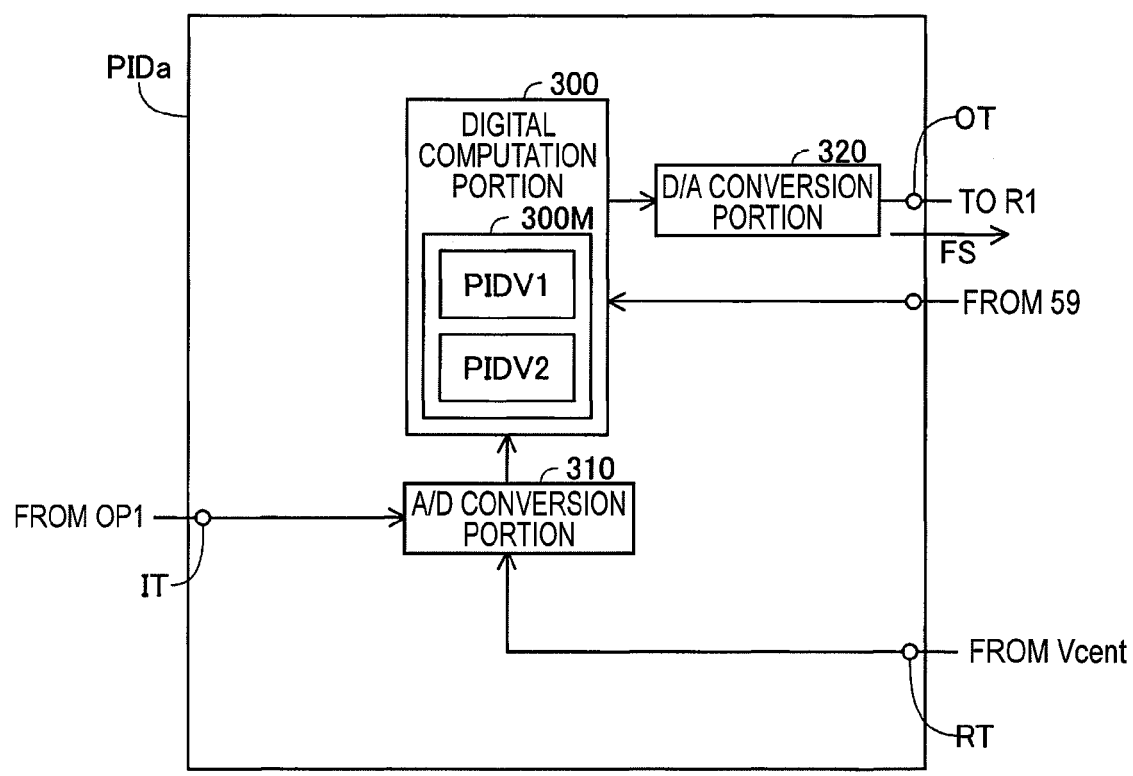
FIG. 11 is an explanatory view illustrating another embodiment of the feedback computation unit.

FIG. 11 is an explanatory view illustrating another embodiment of the feedback computation unit. The difference between this feedback computation unit and the feedback computation unit PID illustrated in FIG. 5 lies in that in lieu of the analog computation circuit, it has a digital computation unit 300 that performs digital computation. The feedback computation unit PIDa has the same function as that of the feedback computation unit PID illustrated in FIG. 5. The feedback computation unit PIDa may be used in the first embodiment in lieu of the feedback computation unit PID.

The feedback computation unit PIDa includes the digital computation unit 300, an A/D conversion portion 310 and a D/A conversion portion 320. As the digital computation unit 300, a computer that has a CPU and a memory may be employed. Moreover, a special-purpose digital computation circuit may be employed. The A/D conversion portion 310 converts an analog signal into digital data. The D/A conversion portion 320 converts digital data into an analog signal.

The signal supplied to the input terminal IT and the signal supplied to the reference terminal RT are converted into digital data by the A/D conversion portion 310. The A/D conversion portion 310 supplies the digital data to the digital computation unit 300. The digital computation unit 300 generates digital data that represents the feedback signal FS from the received data in accordance with predetermined digital computation (PID computation). The digital computation unit 300 supplies the generated data to the D/A conversion portion 320. The D/A conversion portion 320 converts the received data into the feedback signal FS. Then, the D/A conversion portion 320 outputs the feedback signal FS through the output terminal OT.

The digital computation unit 300 includes a memory 300M. The memory 300M has stored therein a value PIDV1 that represents the first control constant and a value PIDV2 that represents the second control constant. In steps S350 and S360 of FIG. 7, the constant control module M4 (FIG. 6) supplies an instruction representing the value to be used among the values PIDV1 and PIDV2 to the feedback computation unit PIDa via the circuit controller 59 (FIG. 1). The digital computation unit 300 uses a value designated by the received instruction. A non-volatile memory is preferably employed as the memory 300M.

In this manner, the current Ip may be feedback-controlled by the digital computation. The control constant that changes in accordance with the temperature may be represented by one value or may be represented by a combination of plural values. For example, the proportional gain used for the P-computation may be changed in accordance with the temperature. Moreover, the combination of the proportional gain used for the P-computation and the integral gain used for the I-computation may be changed in accordance with the temperature. In addition, the constant control module M4 may determine the constant value in accordance with the temperature and supply the constant value thus determined to the feedback computation unit PIDa instead of specifying the constant value to be used from among a plurality of kinds of constant values that are assigned in advance. In either case, the constant control module M4 changes the constant value used for the digital computation.

C. Modifications

The present invention is not limited to the above-described examples or embodiments, but may be practiced in various forms within the spirit and scope of the invention. For example, the following modifications may be adopted.

Modification 1

In the above-described respective embodiments, the computation for feedback control is not limited to PID computation, but various computations capable of implementing a control responsive to the voltage Vs of the current Ip may be employed. For example, P-computation may be employed, and moreover, PI-computation may be employed. Moreover, the computation is not limited to the PID computation and other computations may be employed.

Modification 2

In the above-described respective embodiments, the configuration of the device controlling the gas sensor 5 is not limited to the configuration illustrated in FIG. 1, but various configurations may be employed. For example, a special-purpose amplifier circuit may be used in lieu of the operational amplifier. Moreover, the configuration of the feedback computation unit is not limited to the configurations illustrated in FIGS. 5 and 11, but various configurations may be employed.

Moreover, the configuration for changing the control constant of the feedback control is not limited to the configurations illustrated in FIGS. 5 and 11, and various configurations may be employed. For example, the feedback computation unit PID illustrated in FIG. 5 may change the resistance value between the two nodes P2 and Pout by turning a switch On/Off. Moreover, instead of changing the resistance value, the capacitance of a capacitor or the inductance of a coil may be changed. In either case, by using a switch (for example, the switch SWp) capable of changing the connection state between the analog computation circuit (for example, the control operational amplifier 140) and the circuit elements (for example, resistors, capacitors, or coils), the control constant of the computation by the analog computation circuit can be changed appropriately.

Furthermore, as the constant that is changed in accordance with the temperature, various control constants for feedback control may be employed. Here, the control constants of the feedback control refer to parameters that determine the responsiveness of the feedback control. Examples of such parameters include the proportional gain of the P-computation, the integral gain of the I-computation, the differential gain of the D-computation, and the like.

Modification 3

In the above-described respective embodiments, the number of steps of the control constant that is changed in accordance with the temperature may be three or more. For example, in the embodiment illustrated in FIG. 7, the control constant may be replaced with a second threshold temperature lower than the threshold temperature TT. In either case, the control constant may be experimentally determined in advance so as to adapt to frequency characteristics at various temperatures under which a gas sensor is actually used.

Modification 4

In the above-described respective embodiments, the procedures for the sensor control process are not limited to the procedures illustrated in FIGS. 7, 9 and 10, but various procedures may be employed. For example, the process (the process of FIG. 10) of measuring the impedance of the electromotive force cell 24 may be executed independent of control (FIG. 9) of the heater 80. For example, the process of FIG. 10 may be executed when the constant control module M4 instructs the circuit controller 59 (FIG. 1) to start measurement of the element impedance in step S330 of FIG. 7.

Modification 5

In the above-described respective embodiments, the indicative value that correlates with the resistance value of the electromotive force cell 24 is not limited to the voltage that is obtained by feeding a constant current through the electromotive force cell 24, and various values may be employed. For example, a current that is obtained by applying a constant voltage to the electromotive force cell 24 may be employed. In either case, the corresponding relationship between the indicative value and the temperature of the gas sensor may be experimentally determined in advance.

In the above-described respective embodiments, the value (the corresponding temperature value) that corresponds to the temperature of the gas sensor 5 is not limited to the impedance, but various values (for example, admittance) that vary in accordance with the temperature of the gas sensor 5 may be employed. That is to say, various values representing the temperature of the gas sensor 5 may be used as the corresponding temperature value. These values correlate with the temperature of the gas sensor 5. For example, a temperature sensor may be attached to the gas sensor 5 and an output of the temperature sensor may be used. In this case, the temperature sensor corresponds to the "acquisition unit" that acquires a value corresponding to the temperature of the gas sensor. Moreover, the temperature sensor may be attached to an arbitrary portion of the gas sensor 5. However, the temperature sensor is preferably attached to at least one of the first solid electrolyte and the second solid electrolyte.

Moreover, the process for changing the control constant in accordance with the corresponding temperature value is not limited to the process illustrated in FIG. 7, but various processes may be employed. For example, the control constant of the feedback control may be changed independent of the control of the current Ip. It is generally preferable that, when the corresponding temperature value is acquired and the corresponding temperature value indicates that the temperature of the gas sensor is within the first temperature range, the first control constant is used, whereas when the corresponding temperature value indicates that the temperature of the gas sensor is within the second temperature range, the second control constant is used. The condition for determining that the corresponding temperature value indicates that the temperature of the gas sensor is in the first temperature range may be experimentally determined in advance in accordance with the corresponding temperature value that is actually used. For example, the corresponding temperature value may be compared with at least one of a predetermined first threshold value that corresponds to the upper limit of the first temperature range and a predetermined second threshold value that corresponds to the lower limit of the first temperature range. The same can be applied to the determination condition for the second temperature range.

Moreover, as the process for controlling the heater 80, similar to the embodiment illustrated in FIG. 9, the process based on the corresponding temperature value may be employed. Alternatively, the heater may be controlled independent of the corresponding temperature value that is used for changing the control constant of the feedback control. For example, the control constant of the feedback control may be changed in accordance with the corresponding temperature value (for example, impedance) and the heater 80 may be controlled in accordance with the output signal of the temperature sensor attached to the gas sensor 5. Moreover, the heater 80 may be repeatedly turned On/Off at timings experimentally determined in advance so that the temperature of the gas sensor is increased to the target temperature.

Modification 6

In the above-described respective embodiments, the gas sensor is not limited to the air-fuel ratio sensor illustrated in FIG. 2, but various sensors that have a measurement chamber, a pump cell, and an electromotive force cell may be employed. For example, the heater 80 may be omitted in the embodiment illustrated in FIG. 2. Moreover, a sensor (which is also referred to as an NOx sensor) that measures the concentration of nitrogen oxides (NOx) in the exhaust gas may be employed. The NOx sensor may have a configuration such that a second measurement chamber and a second pump cell are added to the gas sensor 5 in FIG. 2. The NOx sensor may be operated in the following manner, for example. An exhaust gas is introduced into the measurement chamber 20 (FIG. 2). The oxygen concentration in the measurement chamber 20 is adjusted to a predetermined concentration by feedback control based on the voltage Vs of the current Ip. Exhaust gas in which the oxygen concentration has been adjusted is introduced into the second measurement chamber (not illustrated). One electrode of the second pump cell is exposed to the second measurement chamber. The NOx introduced into the second measurement chamber is decomposed on the electrode, and as a result, oxygen is produced. When a voltage is applied to the second pump cell, a current flows which corresponds to the amount of oxygen production. By measuring this current, the amount (i.e., concentration) of NOx can be determined.

In either case, the respective electrodes of the pump cell and the electromotive force cell preferably contain a catalyst (for example, platinum or palladium). By doing so, the respective cells can easily perform operations making use of the movement of oxygen ions in the electrolyte.

Modification 7

In the above-described respective embodiments, a part of the configurations realized by hardware may be replaced with software, and conversely, a part or the whole of the configurations realized by software may be replaced with hardware. For example, the function of the constant control module M4 in FIG. 6 may be realized by a special-purpose hardware circuit.

Moreover, when a part or the whole of the functions of the present invention is realized by software, the software (computer program) may be provided in a form such that it is stored in a computer-readable recording medium. In the present invention, "computer-readable recording medium" is not limited to a portable recording medium such as flexible disk or CD-ROM, and it includes an internal storage device provided inside a computer, such as RAM or ROM, or an external storage device attached to a computer, such as hard disc.

The present invention can be embodied in various forms such as, for example, a method for controlling a gas sensor, an apparatus for controlling a gas sensor, a gas sensor system having such a control apparatus and such a gas sensor, a computer program for realizing the functions of such a method or apparatus, and a recording medium recording such a computer program.

It should further be apparent to those skilled in the art that the various changes in form and detail of the invention as shown and described above may be made. It is intended that such changes be included within the spirit and scope of the claims appended hereto.

This application claims priority from Japanese Patent Application No. 2008-293187, filed on Nov. 17, 2008, the disclosure of which is incorporated by reference in its entirety.

What is claimed is:

1. A gas sensor system comprising:
a gas sensor;
a heater that is used for raising a temperature of the gas sensor to a target temperature;
a current control unit;
a constant control unit; and
an acquisition unit that acquires a corresponding temperature value which is a value corresponding to the temperature of the gas sensor, wherein:
the gas sensor comprises:
a measurement chamber into which a measurement target gas is introduced:
a pump cell comprising, a first outer electrode, a first inner electrode that is exposed to the measurement chamber, and a first solid electrolyte that is interposed between the first outer electrode and the first inner electrode; and
an electromotive force cell comprising a second outer electrode, a second inner electrode that is exposed to the measurement chamber, and a second solid electrolyte that is interposed between the second outer electrode and the second inner electrode;
the current control unit performs a feedback control on a current flowing through the pump cell in response to a voltage of the electromotive force cell and in accordance with a control constant which characterizes the feedback control;
the constant control unit changes the control constant based on the corresponding temperature value; and
the constant control unit is configured to adopt:
a predetermined first control constant when the corresponding temperature value indicates that the temperature of the gas sensor is within a first temperature range where a threshold temperature lower than the target temperature is an upper limit of the first temperature range and an activating temperature of the gas sensor is a lower limit of the first temperature range; and
a predetermined second control constant different from the first control constant when the corresponding temperature value indicates that the temperature of the gas sensor is within a second temperature range, the second temperature range including the target temperature and where a temperature higher than the threshold temperature is a lower limit of the second temperature range,
wherein the constant control unit is configured to adopt the first control constant instead of the second control constant when the corresponding temperature value indicates that the temperature of the gas sensor is within a first temperature range, and
wherein the predetermined first control constant has a constant, non-changing value over the first temperature range, and the predetermined second control constant has a constant, non-changing value over the second temperature range.

2. The gas sensor system according to claim 1, wherein:
the current control unit comprises:
a plurality of circuit elements that may be differently configured to define different control constants; and
an analog computation circuit that executes computation for the feedback control based on a control constant defined by the circuit elements; and,
the constant control unit comprises
a switch that changes the control constant by switching a connection state between the analog computation circuit and the plurality of circuit elements.

3. The gas sensor system according to claim 1, wherein:
the current control unit comprises
a computation unit that executes digital computation for the feedback control based on a constant value representing the control constant; and,
the constant control unit changes the constant value used for the digital computation.

4. The gas sensor system according to claim 1, wherein:
the acquisition unit acquires, as the corresponding temperature value, an indicative value that correlates with a resistance value of the electromotive force cell; and,
the constant control unit changes the control constant in accordance with the indicative value.

5. The gas sensor system according to claim 1, wherein:
the current control unit performs feedback control on the current flowing through the pump cell so that the voltage of the electromotive force cell becomes a target voltage.

6. The gas sensor system according to claim 1, wherein the constant control unit performs feedback control in accordance with two or more control constants which characterize the feedback control, and the constant control unit changes at least one of the control constants based on the corresponding temperature value.

7. A method for controlling a gas sensor, wherein:
the gas sensor comprises:
a measurement chamber into which a measurement target gas is introduced;
a pump cell comprising, a first outer electrode, a first inner electrode that is exposed to the measurement chamber, and a first solid electrolyte that is interposed between the first outer electrode and the first inner electrode; and
an electromotive force cell comprising, a second outer electrode, a second inner electrode that is exposed to the measurement chamber, and a second solid electrolyte that is interposed between the second outer electrode and the second inner electrode; and
the method comprises:
performing a feedback control on a current flowing through the pump cell in response to a voltage of the electromotive force cell and in accordance with a control constant which characterizes the feedback control;
acquiring a corresponding temperature value which is a value corresponding to a temperature of the gas sensor;
changing the control constant in accordance with the corresponding temperature value; and
raising the temperature of the gas sensor to a target temperature; and
wherein the step of changing the control constant comprises:
adopting a predetermined first control constant when the corresponding temperature value indicates that the temperature of the gas sensor is within a first temperature range where a threshold temperature lower than the target temperature is an upper limit of the first temperature range and an activating temperature of the gas sensor is a lower limit of the first temperature range; and
adopting a predetermined second control constant different from the first control constant when the corresponding temperature value indicates that the temperature of the gas sensor is within a second temperature range, the second temperature range including the target temperature and where a temperature higher than the threshold temperature is a lower limit of the second temperature range,
wherein a constant control unit adopts the first control constant instead of the second control constant when the corresponding temperature value indicates that the temperature of the gas sensor is within a first temperature range, and
wherein the predetermined first control constant has a constant, non-changing value over the first temperature range, and the predetermined second control constant has a constant, non-changing value over the second temperature range.

8. The method according to claim 7, wherein an analog computation circuit executes computation for the feedback control based on a control constant, which control constant is defined by a plurality of circuit elements that may be differently configured to define different control constants; and the step of changing the control constant comprises switching a connection state between the analog computation circuit and the plurality of circuit elements.

9. The method according to claim 7, wherein a computation unit executes digital computation for the feedback control based on a constant value representing the control constant; and,
the step of changing the control constants comprises changing the constant value used for the digital computation.

10. The method according to claim 7, wherein:
the step of acquiring the corresponding temperature value comprises acquiring, as the corresponding temperature value, an indicative value that correlates with a resistance value of the electromotive force cell; and,
the step of changing the control constants comprises changing the control constants in accordance with the indicative value.

11. The method according to claim 7, wherein:
the step of performing the feedback control on the current comprises performing feedback control on the current flowing through the pump cell so that the voltage of the electromotive force cell becomes a target voltage.

12. The method according to claim 7, which comprises performing feedback control in accordance with two or more control constants which characterize the feedback control, and changing at least one of the control constants based on the corresponding temperature value.

* * * * *